(12) United States Patent
Bailey et al.

(10) Patent No.: US 10,182,827 B2
(45) Date of Patent: Jan. 22, 2019

(54) SURGICAL INSTRUMENT

(71) Applicant: DEPUY IRELAND UNLIMITED COMPANY, Cork (IE)

(72) Inventors: Andrew Bailey, Leeds (GB); James Brooks, Leeds (GB)

(73) Assignee: DEPUY IRELAND UNLIMITED COMPANY, Cork (IE)

(*) Notice: Subject to any disclaimer, the term of this patent is extended or adjusted under 35 U.S.C. 154(b) by 197 days.

(21) Appl. No.: 15/111,528

(22) PCT Filed: Feb. 17, 2015

(86) PCT No.: PCT/GB2015/050445
§ 371 (c)(1),
(2) Date: Jul. 14, 2016

(87) PCT Pub. No.: WO2015/124912
PCT Pub. Date: Aug. 27, 2015

(65) Prior Publication Data
US 2016/0324529 A1    Nov. 10, 2016

(30) Foreign Application Priority Data
Feb. 20, 2014   (GB) .................................. 1403020.9

(51) Int. Cl.
*A61B 17/15* (2006.01)
*A61B 17/00* (2006.01)

(52) U.S. Cl.
CPC ............ *A61B 17/15* (2013.01); *A61B 17/154* (2013.01); *A61B 17/155* (2013.01); *A61B 2017/00862* (2013.01)

(58) Field of Classification Search
CPC ..... A61B 17/15; A61B 17/154; A61B 17/155; A61B 17/157
See application file for complete search history.

(56) References Cited

U.S. PATENT DOCUMENTS 5,415,663 A * 5/1995 Luckman ............... A61B 17/15
                                                606/86 R
5,445,642 A    8/1995 McNulty et al.
(Continued)

FOREIGN PATENT DOCUMENTS

EP            914806 B1    1/2004

OTHER PUBLICATIONS

LCS® High Performance Instruments Surgical Technique, Product Information Sheet by Depuy International, 0612-90-510, 2010, 42 Pages.
(Continued)

*Primary Examiner* — Matthew Lawson (57) ABSTRACT

A cutting block comprises a body having a top surface for guiding a saw blade, and a top plate connected to the body. The top plate can move between a first position in which the top plate is spaced apart from the body and a second position in which the top surface of the top plate is an extension of the top surface of the body. The top plate has first and second resiliently deformable arms extending from it, spaced apart along the top plate, and the body has first and second recesses formed in it extending substantially perpendicularly to the top surface of the body. The first and second arms on the top plate are inserted in the recesses so that the arms and the recesses define the path for movement of the top plate relative to the body between the first and second position.

3 Claims, 10 Drawing Sheets

(56) References Cited

U.S. PATENT DOCUMENTS

| | | | |
|---|---|---|---|
| 5,597,379 A * | 1/1997 | Haines | A61B 17/1764 |
| | | | 606/80 |
| 5,749,876 A * | 5/1998 | Duvillier | A61B 17/155 |
| | | | 606/86 R |
| 6,174,314 B1 | 1/2001 | Waddell | |
| 6,755,839 B2 | 6/2004 | Van Hoeck et al. | |
| 7,364,581 B2 | 4/2008 | Michalowicz | |
| 8,038,681 B2 | 10/2011 | Koenemann | |
| 8,518,048 B2 | 8/2013 | Shelke | |
| 8,579,906 B2 | 11/2013 | Rangaiah | |
| 9,028,501 B2 | 5/2015 | Thomas | |
| 9,050,107 B2 | 6/2015 | Sordelet et al. | |
| 9,113,913 B2 | 8/2015 | Reeve | |
| 9,271,739 B2 | 3/2016 | Young | |
| 2006/0142774 A1 | 6/2006 | Metzger | |
| 2013/0325016 A1* | 12/2013 | Sordelet | A61B 17/155 |
| | | | 606/87 |
| 2014/0296929 A1 | 10/2014 | Stacey | |
| 2015/0038975 A1* | 2/2015 | Kumar | A61B 17/155 |
| | | | 606/88 |
| 2016/0128702 A1 | 5/2016 | Grant et al. | |

OTHER PUBLICATIONS

International Search Report for Corresponding International Application No. PCT/GB2015/050445 dated May 7, 2015, 10 Pages.
UK Search Report for Corresponding Application No. GB1403020.9, dated Aug. 13, 2014, 3 Pages.
Chinese Search Report for Corresponding App. No. 2015800009413.9, dated Jun. 16, 2018, 4 Pages.

* cited by examiner

SURGICAL INSTRUMENT

CROSS REFERENCE TO RELATED APPLICATION

This application is a National Stage 35 U.S.C. 371 of International Patent Application PCT/GB2015/050445 filed Feb. 17, 2015, claiming priority to United Kingdom applications GB1403020.9, filed Feb. 20, 2014 (now abandoned).

BACKGROUND OF THE INVENTION

The present invention relates to surgical instruments and in particular to surgical instruments that include guiding surfaces for saws and other cutting tools used in bone surface preparation.

Many surgical instruments are fixed in a known position relative to a patient, particularly when used in bone surface preparation. One example is a cutting block. Cutting blocks are typically affixed to a patient's bone in a position such that they can guide cutting and resection of the bone surface for receiving an implant.

Existing cutting blocks may include a guide, recess or cutting groove for the cutting tool, such as a saw, used for cutting and resectioning in order to correctly position and guide the cutting tool during the surgical procedure.

In an existing cutting block, the cutting block has a top surface for guiding a saw blade during a step in an orthopaedical surgical procedure, such as distal femoral resection. The cutting block also includes a top plate which defines a cutting groove for receiving the saw and which can also be used as a guide during distal femoral resectioning. To achieve this, the top plate is movable between an extended, first position to a closed, second position. In the first position, the top plate defines the cutting groove. When the top plate is in the second position, the top plate is contiguous with a main body of the cutting block to define a top, distal surface for guiding the cutting tool. A surgeon can use either the top surface or the cutting groove as a guide for the cutting tool. The choice of either the top surface or the cutting groove is usual one of personal preference for the surgeon.

Historically, the top plate is locked into the first and second positions by means of two pins with indents which act against a spring loaded ball bearing which indexes the position of the plate with respect to the main body of the cutting block.

BRIEF SUMMARY OF THE INVENTION

According to a first aspect of the invention, there is provided a cutting block for fixing relative to a bone for guiding a saw blade during a step in an orthopaedic surgical procedure in which the bone is cut, the cutting block comprising:
  a. a body having a top surface for guiding a saw blade,
  b. a top plate which is connected to the body and which can move between a first position in which the top plate is spaced apart from the body and a second position in which the top surface of the top plate is contiguous with and an extension of the top surface of the body,
    in which the top plate has first and second resiliently deformable arms extending from it, spaced apart along the top plate, and in which the body has first and second recesses formed in it extending substantially perpendicularly to the top surface of the body, in which the first and second arms on the top plate can be received so that the arms and the recesses define the path for movement of the top plate relative to the body between the first and second positions,
    and in which each of the recesses has a profiled surface against which the respective deformable arm acts during movement of the top plate relative to the body between the first and second positions so as to cause the arm to deform, the deformation of each of the arms being greater when the top plate is in an intermediate position between the first and second positions than when it is in each of the first and second positions, so that the top plate is biased away from the intermediate position towards the first and second positions.

The biasing of the arms to the first and second positions locks the top plate in either the first or second positions.

Providing a cutting block with the features provide for easier manufacturing, particularly as the numbers of components is reduced. Furthermore, it reduces the need for welding with the attendant heat distortion that can affect the final product. The cutting block is also easier to clean Each of the first and second arms may have a pin extending transversely from it, and in which the profiled surfaces are acted against by the pins.

Each of the profiled surfaces may be provided by a groove which is cut in a wall of the body.

The provision of the pins on the arms and which are retained in grooves means that, should the arms become removed from the top plate, they are retained within the cutting block and do not become dislodged and find themselves becoming lodged in surrounding tissue.

Each of the grooves may be curved when viewed in the direction which is defined by the pin which slides in the groove.

Alternatively, the grooves may have a V-shaped configuration, or may be substantially linear and provided with indents at either end to retain the pins at either end of the groove.

As a further alternative, the grooves may be provided with a ridged profile to retain the pins at either end of the groove.

The recesses may be shaped so that each of the arms within its recess in the body is exposed, allowing a user to apply force to the arm to cause the arm to be deformed resiliently to facilitate movement of the top plate between its first and second positions.

The arms may be provided with buttons at the distal end against which manual pressure may be made to deform the arms. The buttons may have a ridged surface to assist with manual purchase against the buttons.

The top surface may have a raised lip and a pair of projections configured to define an inner guiding surface.

The top surface may have a recess configured to accommodate the raised lip and a pair of apertures configured to receive respective ones of the pair of projections.

According to a another aspect of the invention, there is provided a cutting block for fixing relative to a bone for guiding a saw blade during a step in an orthopaedic surgical procedure in which the bone is cut, the cutting block comprising:
  a. a body having a top surface for guiding a saw blade,
  b. a top plate which is connected to the body and which can move between a first position in which the top plate is spaced apart from the body and a second position in which the top surface of the top plate is contiguous with and an extension of the top surface of the body,
    in which the top plate has first and second resiliently deformable arms extending from it, spaced apart along the top plate, and in which the body has first and second recesses formed in it generally transverse to the top surface of the body, in which the first and second arms on the top plate can be received so that the arms and the recesses define the path for movement of the top plate relative to the body between the first and second positions, and in which each of the recesses has a profiled surface against which the respective deformable arm acts during movement of the top plate relative to the body between the first and second positions so as to cause the arm to deform, the deformation of each of the arms being greater when the top plate is in an intermediate position between the first and second positions than when it is in each of the first and second positions, so that the top plate is biased away from the intermediate position towards the first and second positions.

The invention will now be described, by way of example only, with reference to the following drawings, of which.

BRIEF DESCRIPTION OF THE DRAWINGS

DETAILED DESCRIPTION OF THE INVENTION

A cutting block 1 comprises a body 2 and a top plate 3.

The body 2 comprises a contoured front face 4, a substantially planar rear face 5, and a top surface 6.

The body 2 includes a main portion 9 with two side portions 10, 11 extending laterally from each side of the main portion 9. The side portions 10, 11 define respective side faces 17, 18 of the body 2.

Figure 12:
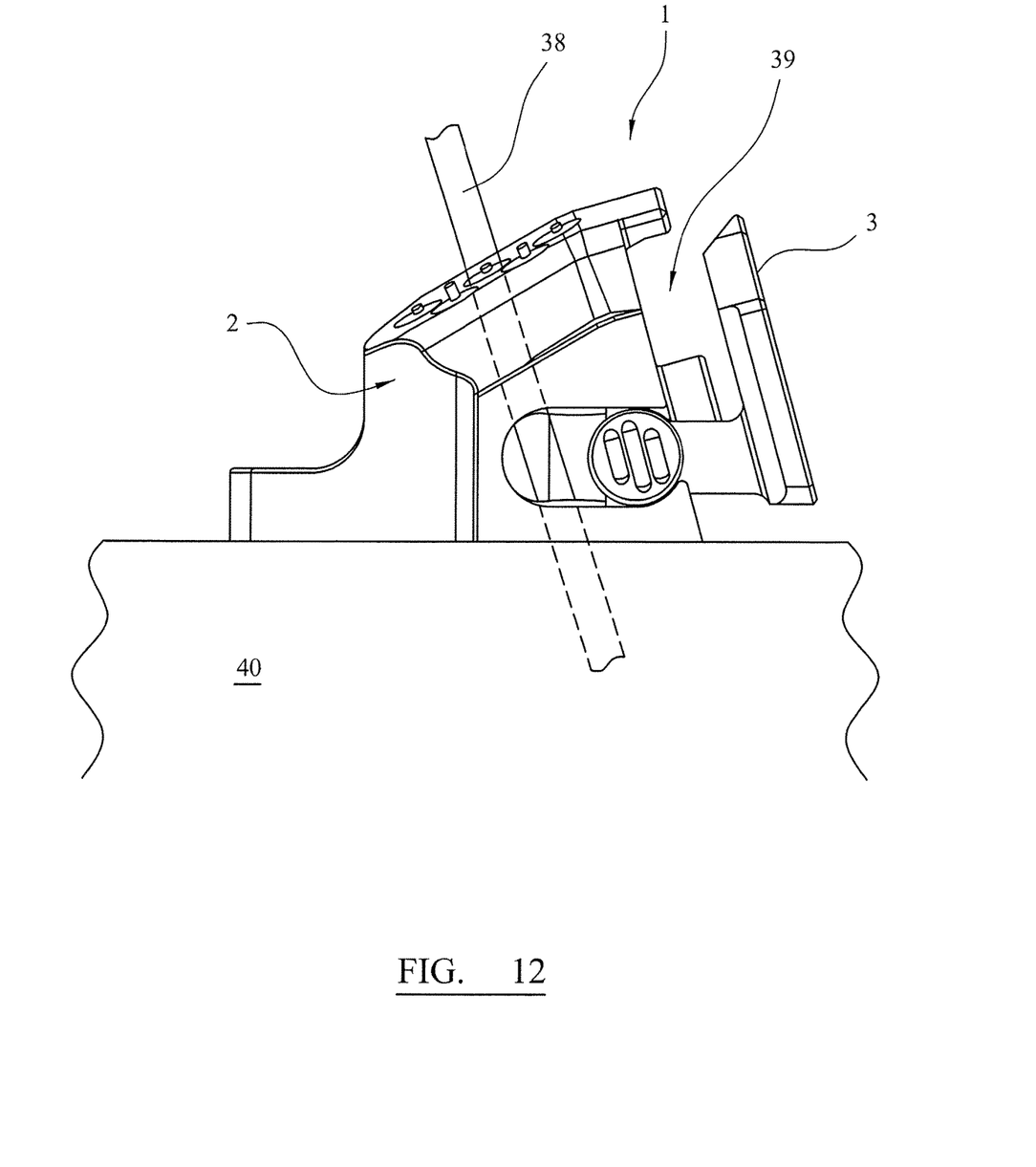
FIG. 12 schematically illustrates the positioning of the cutting block of FIGS. 1 to 11 in place on the distal end of a femur.

The body 2 has a plurality of pairs of spaced apertures 7a, 7b provided in the front face 4 in the main portion 9 with corresponding pairs of spaced apertures 8a, 8b provided in the rear face 5. The pairs of spaced apertures 7a, 7b; 8a, 8b are used to receive a pair of pins 38 to secure the cutting block 1 to the femur 40 as illustrated in FIG. 12 and known to persons skilled in the art.

The main portion 9 of the body 2 has a raised lip 12 on the top face 6 which extends substantially orthogonal to the top surface 6.

The top surface 6 also has a pair of substantially oval-shaped raised projections 13, 14 protruding from the top face 6.

The lip 12 and raised projections 13, 14 define an inner guiding surface 39 used to guide a saw or other cutting tool during distal femoral resection.

Each of the side portions 10, 11 have a substantially U-shaped recess 15, 16 provided therein. Each U-shaped recess 15, 16 opens into the top surface 6 and respective side faces 17, 18 and is generally transverse to the top surface 6 so that they extend substantially perpendicularly to the top surface 6.

Each side portion 10, 11 has a pair of opposed curved grooves 19a, 19b; 20a, 20b, one curved groove of each pair of curved grooves 19a, 19b; 20a, 20b being provided in the respective front face 4 and rear face 5 of the body 2. Each curved groove 19a, 19b; 20a, 20b extends through into the respective recess 15, 16. The ends of each groove 19a, 19b; 20a, 20b define stop surfaces to limit movement of the top plate 3 between first and second positions as will be described in further detail below.

The top plate 3 has an upper face 21 and a lower face 22. The top plate 3 has a front edge 23, rear edge 24 and side edges 25, 26 which are configured such that the outer contour of the top plate 3 substantially matches the top face 6 of the body 2.

The top plate 3 has a recess 27 along the front edge 23 configured to accommodate the raised lip 12 of the body 2. The top plate 3 also has a pair of first and second substantially oval-shaped apertures 28, 29 configured to receive respective protrusions 13, 14 of the body 2. In this way, the top plate 3 can be moved to a position in which it is contiguous with, and an extension of, the top surface 6 of the body 2. In this position the upper surface 21 of the top plate 3 defines a distal surface 37 for the cutting block 1.

A circular aperture 30 is provided in the top plate 3 between the first and second apertures 28, 29.

Extending orthogonally from the lower face 22 of the top plate 3 spaced apart along the top plate 3, towards the side edges 25, 26, are first and second resiliently deformable arms 31, 32. The resiliently deformable arms 31, 32 terminate in a button 33, 34 which serve to facilitate manual deformation of the arms 31, 32 as will be described in further detail below.

Extending transversely, and in opposite directions, from each of the first and second arms 31, 32 are a pair of pins 35a, 35b; 36a, 36b.

The first and second resiliently deformable arms 31, 32 are connected to the top plate 3 by means of a living hinge connection or other suitable means of enabling the deformation.

When assembled, the cutting block 1 comprises the top plate 3 engaged with the body 2. Specifically, the first and second resiliently deformable arms 31, 32 are received in the respective recess 15, 16 and the pins 35a, 35b; 36a, 36b are received into, and engage with, corresponding grooves 19a, 19b; 20a, 20b. The pins 35a, 35b; 36a, 36b are arranged to slide within, and along the length of, the groove 19a, 19b; 20a, 20b with which it is engaged.

The grooves 19a, 19b; 20a, 20b define profiled surfaces of the respective recess 15, 16, and by virtue of engagement of the pins 35a, 35b; 36a, 36b in the grooves 19a, 19b; 20a, 20b, the resiliently deformable arms 25, 26 act against these profiled surfaces.

The resiliently deformable arms 25, 26 and the recesses 15, 16 into which they are received define a path for movement of the top plate 3 relative to the body 2 between a first and a second position as will be described further below.

Figure 1:
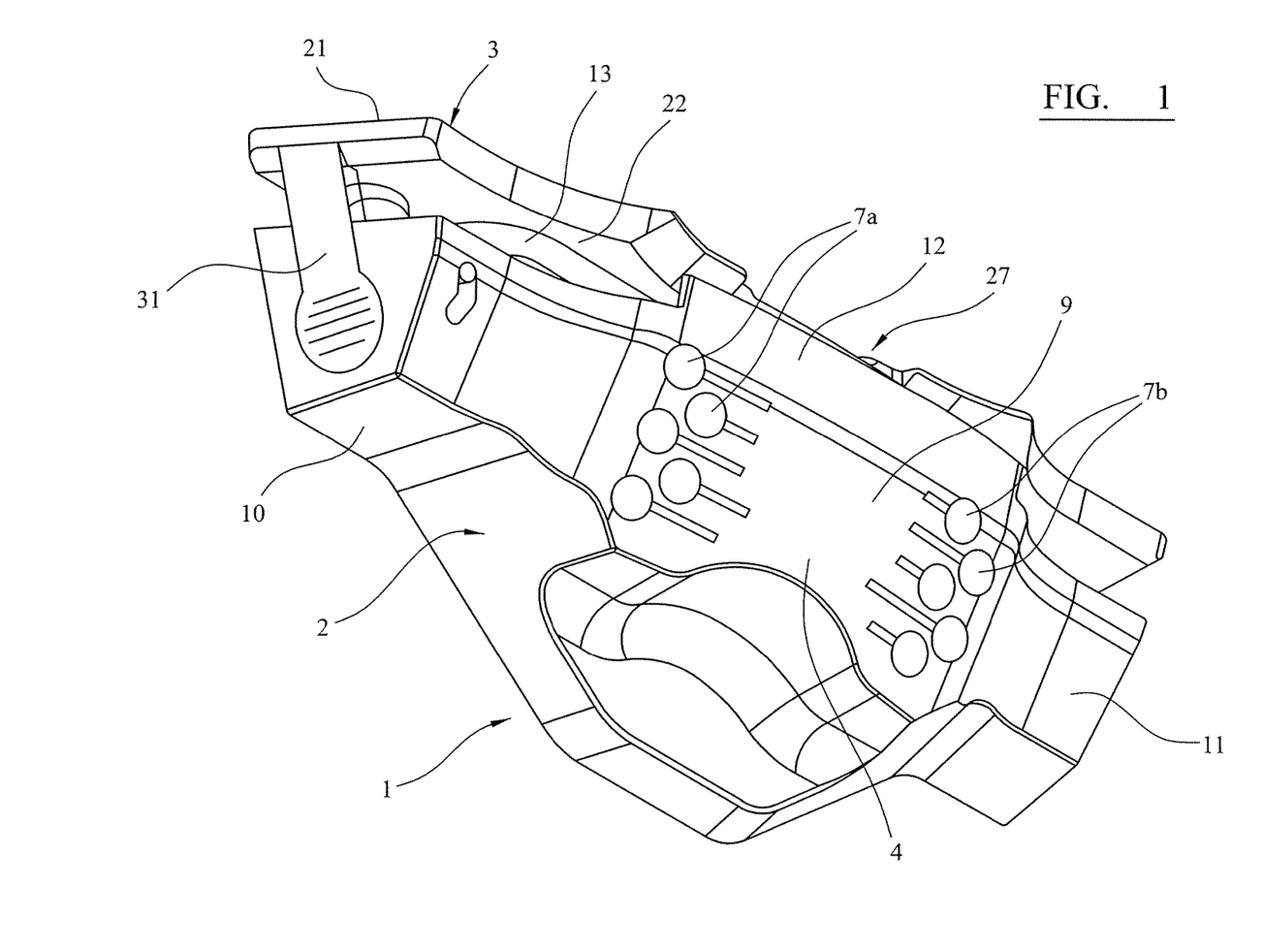
FIG. 1 is a schematic perspective view a cutting block of the invention.
Figure 2:
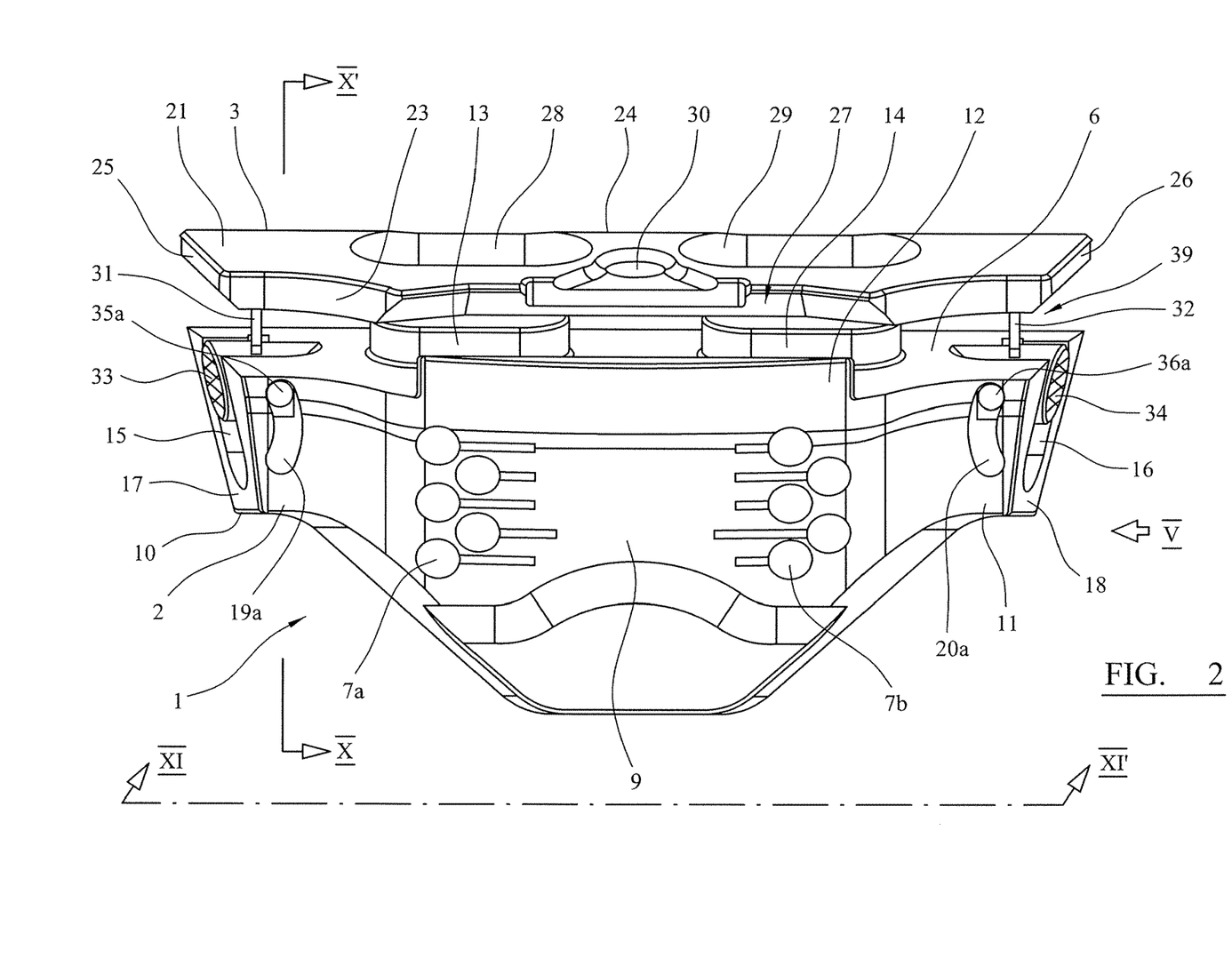
FIG. 2 is a front view of the cutting block of FIG. 1.

In the first position the top plate 3 is spaced apart from the top surface 6 of the body 2 and the pins will be located within the respective groove at a first end of the groove 19a, 19b; 20a, 20b. This is illustrated in FIG. 2.

Figure 3:
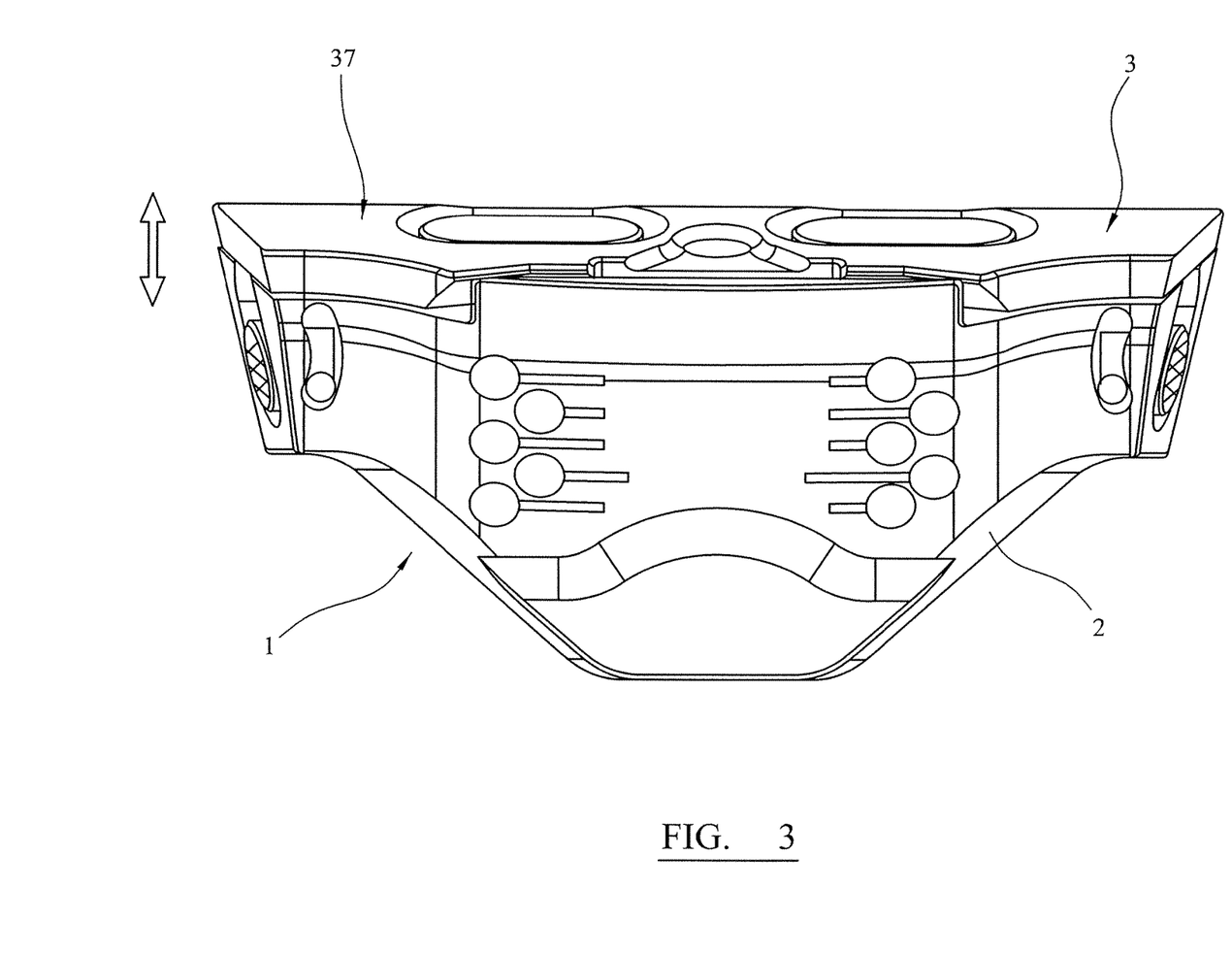
FIG. 3 is a corresponding figure to Figure showing the top plate in a closed position.
Figure 4:
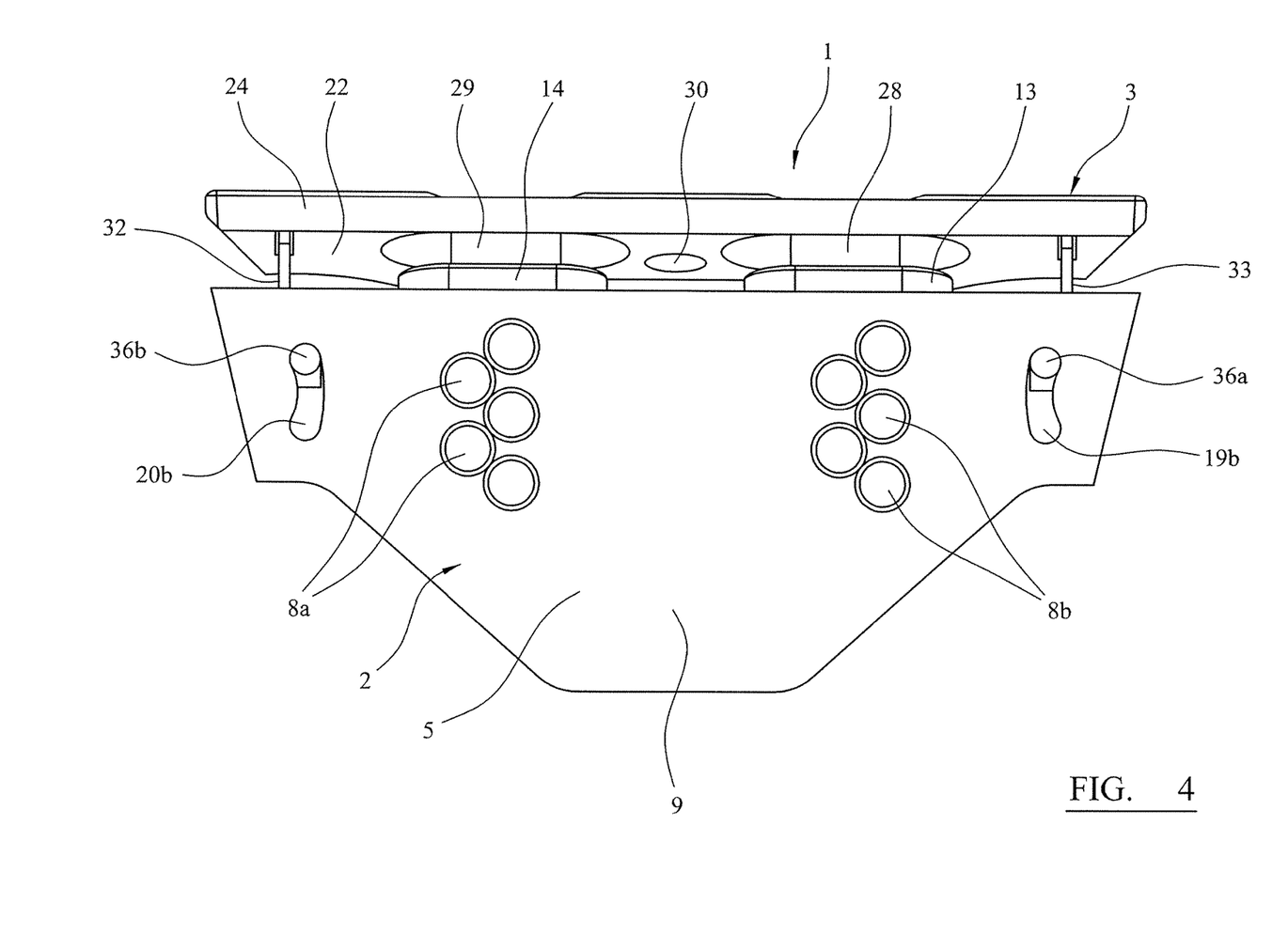
FIG. 4 is a rear view of the cutting block of FIG. 1.
Figure 5:
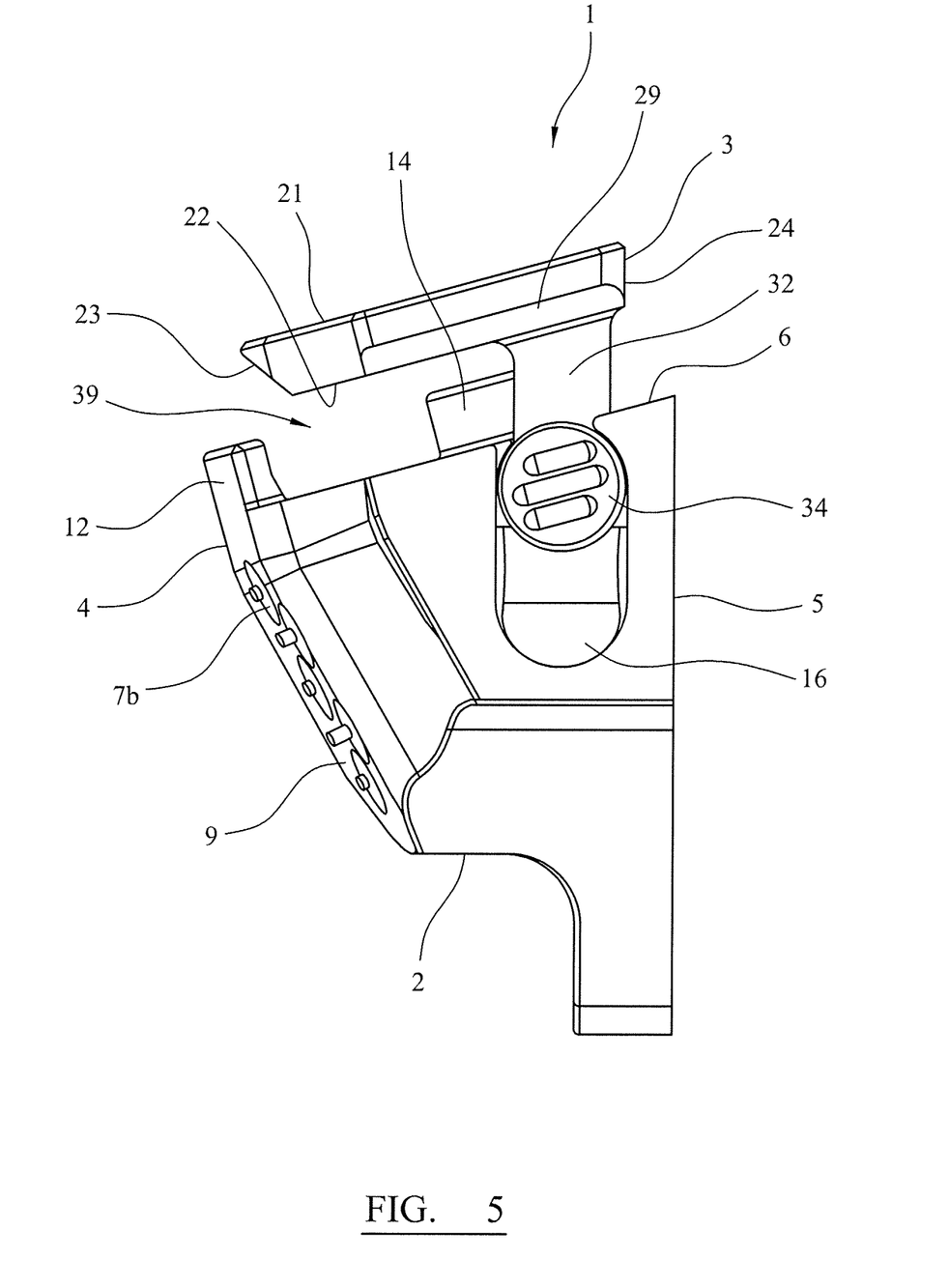
FIG. 5 is a side view of the cutting block of FIG. 1 in the direction of arrow V in FIG. 2.
Figure 6:
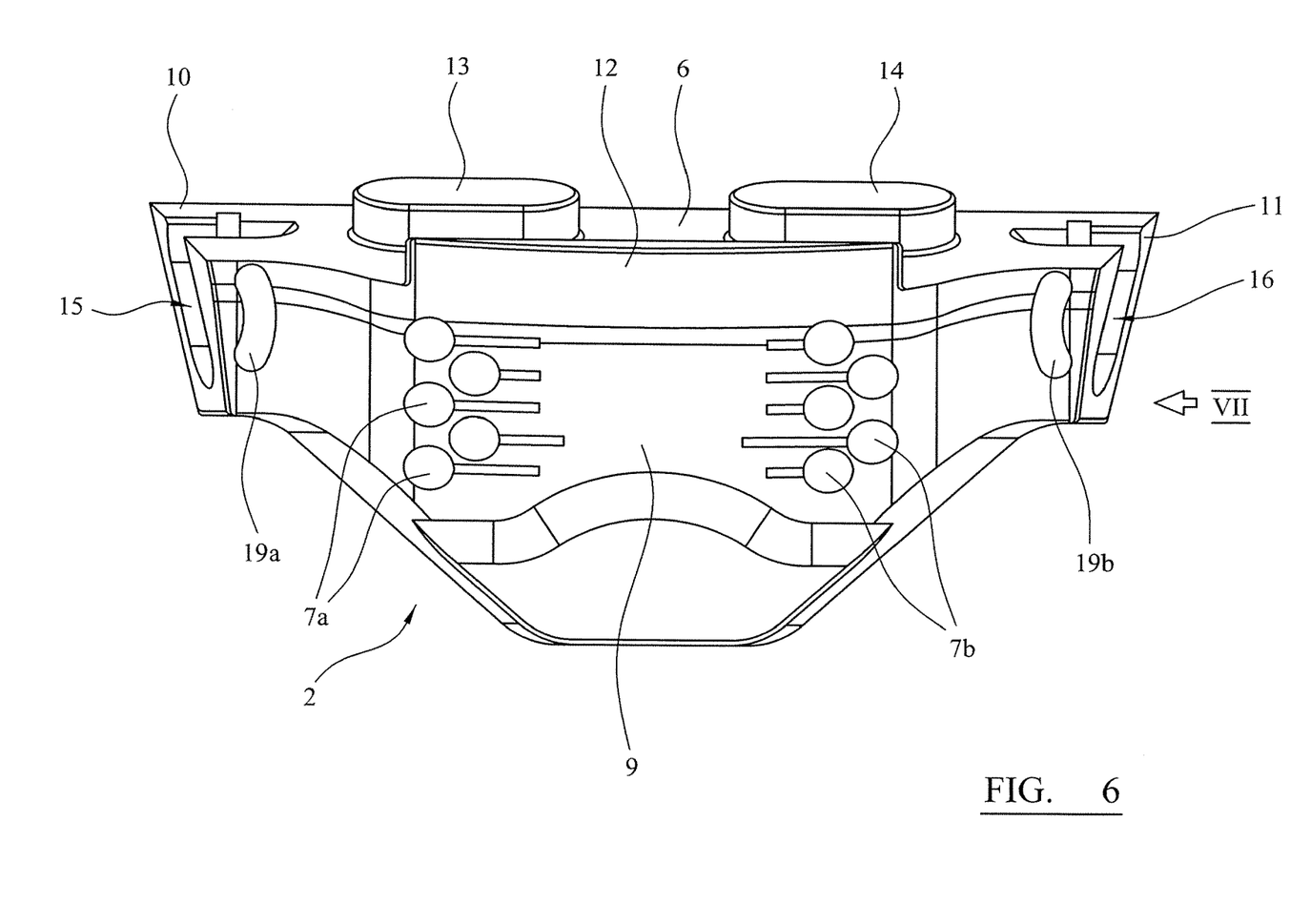
FIG. 6 is a front view of the body of the cutting block of FIG. 1.
Figure 7:
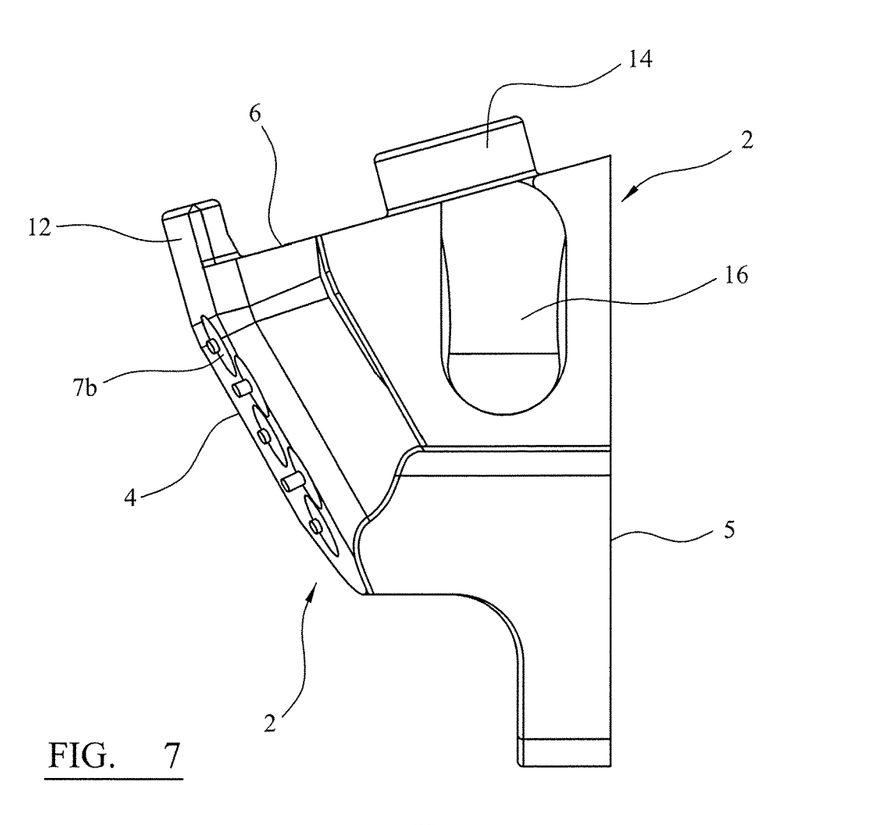
FIG. 7 is a side view of the body of FIG. 6 in the direction of arrow VII.
Figure 8:
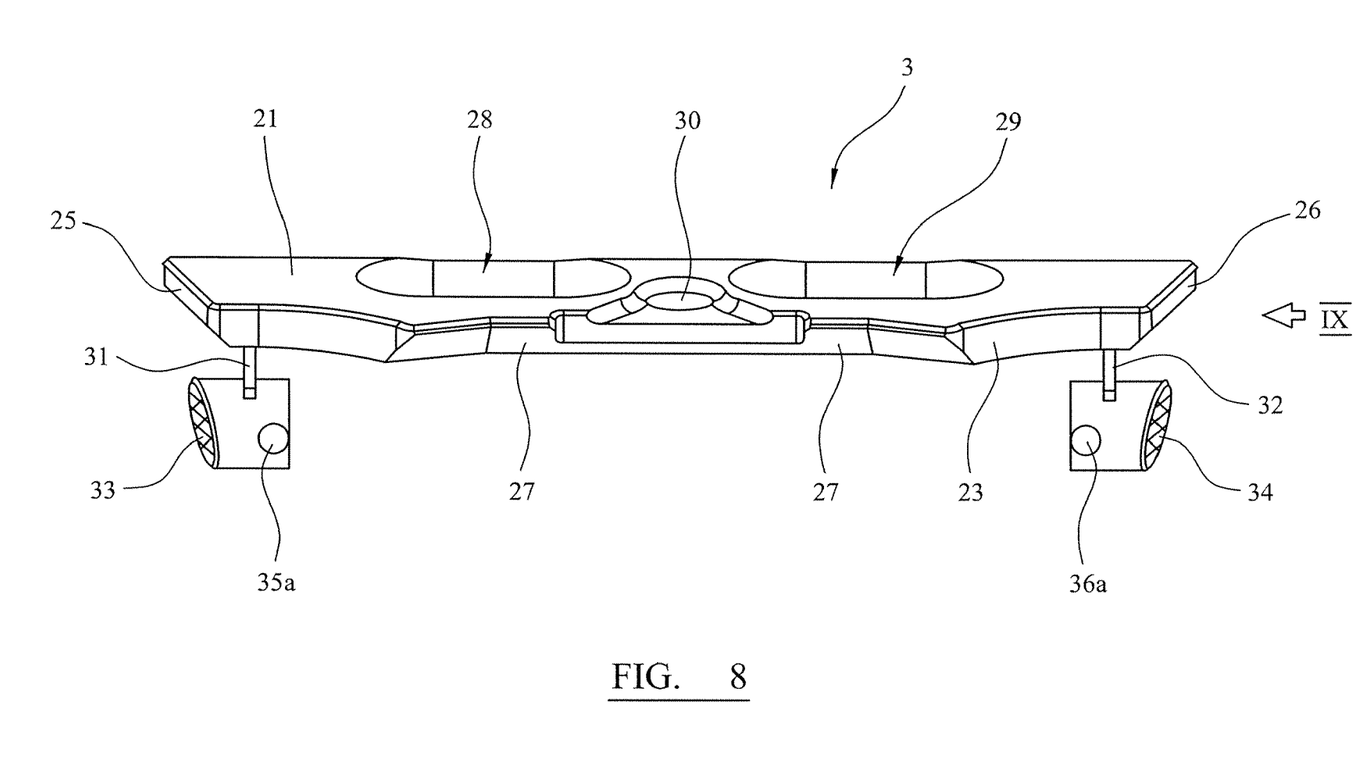
FIG. 8 is a front view of the top plate of the cutting block of FIG. 1.
Figure 9:
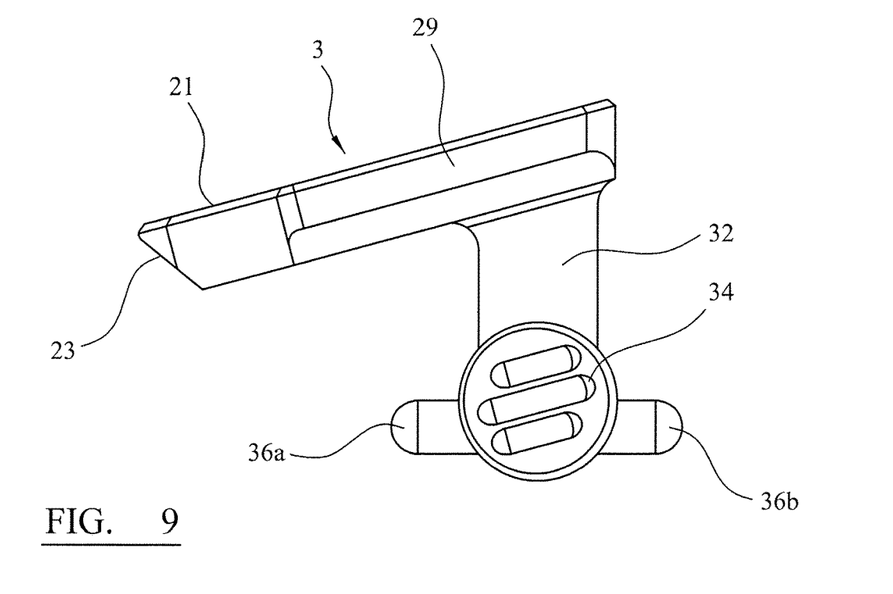
FIG. 9 is a side view of the top plate of FIG. 8 in the direction of arrow IX.
Figure 10:
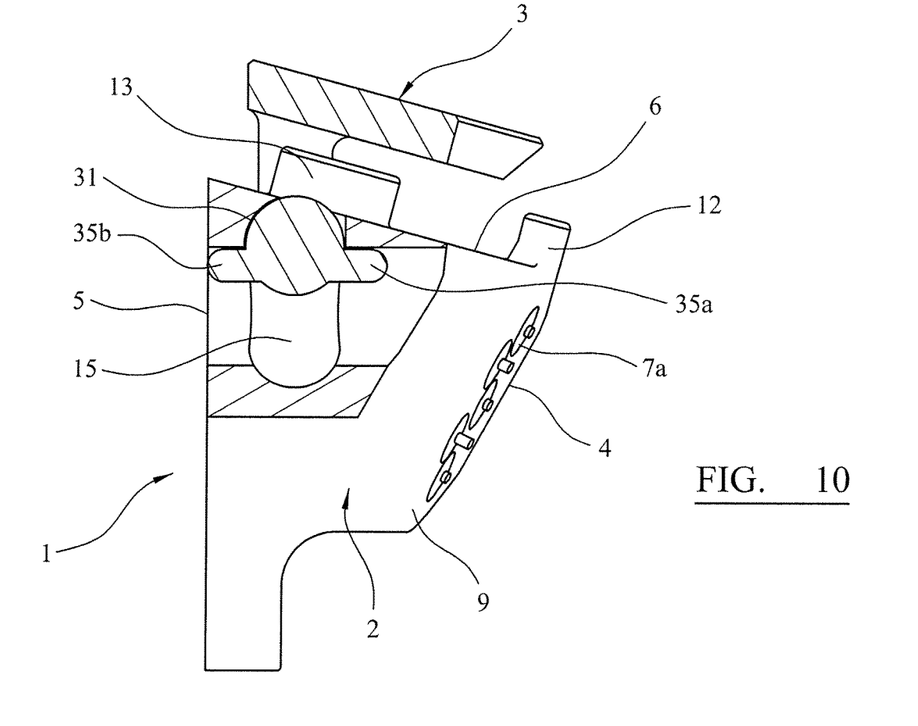
FIG. 10 is cross-section through the cutting block of FIG. 1, in the direction of arrows X-X' of FIG. 2.
Figure 11:
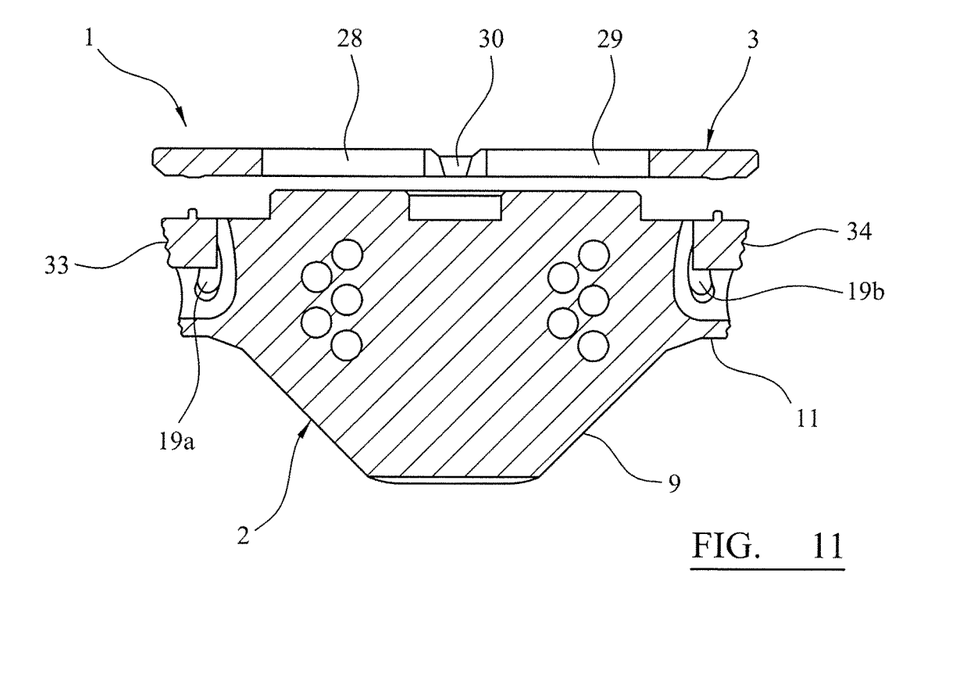
FIG. 11 is a cross-section in the direction of arrows XI-XI' of FIG. 2.

In the second position, the top plate 3 is contiguous with, and an extension of, the top surface 6 of the body 2 and the pins 35a, 35b; 36a, 36b will be at the other, second, end of the respective groove 19a, 19b; 20a, 20b. In the second position, the raised lip 12 of the body 2 is received within the recess 27 of the top plate 3, and the first and second substantially oval-shaped apertures 28, 29 receive respective protrusion 13, 14 of the body 2. In this way, the upper surface 21 is flush with respective protrusions 13, 14 and the top of the raised lip 12 to define the distal surface 37. This is illustrated in FIG. 3.

The ends of the grooves 19a, 19b; 20a, 20b define the stop surfaces limiting movement of the top plate 3 between the first and second positions.

Movement of the top plate 3 relative to the body 2 between the first and second positions causes the resiliently deformable arms 25, 26 to deform as the pins 35a, 35b; 36a, 36b act against the profiled surfaces defined by the grooves 19a, 19b; 20a, 20b.

As the grooves 19a, 19b; 20a, 20b are curved, the deformation of each of the arms 25, 26 is greater when the top plate 3 is in an intermediate position between the first and second positions than when it is in each of the first and second positions. Thus, the top plate 3 is biased away from the intermediate position towards the first and second positions. In this way, the top plate 3 is biased to either the first position or second position so as to remain that position when moved to that position.

To move the top plate 3 between the first and second positions, the top plate 3 is gripped manually and moved between the two positions.

This can be further facilitated by applying manual pressure to the buttons 33, 34, for example by means of a finger and the thumb of one hand, which causes the arms 25, 26 to deform inwardly towards each other facilitates sliding of the pins 35a, 35b; 36a, 36b in the grooves 19a, 19b; 20a, 20b so that the top plate 3 moves between the first position and the second position.

The cutting block 1 of the present invention is for use in knee replacement surgery.

In accordance with known techniques for knee replacement surgery, bone surfaces require preparation in order for the replacement prosthetic to be attached. One of the bone surfaces that require preparation is the distal end of a femur at the knee. The cutting block of the present invention is used in the distal femoral resection step.

In order to carry-out the distal femoral resection, the distal cutting block 1 is mounted onto the distal end of the femur.

Prior to distal femoral resection, anterior and posterior portions, specifically the anterior cortex and the posterior femoral condyles, of the femur are resected in accordance with known techniques.

The cutting block 1 is then mounted on the resected surface of the anterior cortex in order to carry out the distal femoral resection. To mount the distal cutting block 1 onto the distal section of the femur, a distal femoral outrigger is used. An example of this as the distal femoral outrigger of the LCS® Complete™—P.F.C. Sigma™ RP Mobile Bearing Total Knee System manufactured by DePuy Orthopaedics Incorporated.

The distal cutting block 1 is attached to the distal femoral outrigger by means of an attachment mechanism (not shown) which is retained within the circular aperture 30 of the top plate 3. This means of attachment is known to persons skilled in the art and need not be described in any further detail herein.

At this stage, the top plate 3 of the distal cutting block 1 is in the first position, the top plate being moved to this position by manual force applied to the top plate 3 and with further manual pressure applied to the buttons 33, 34 if required.

Because the grooves 19a, 19b; 20a, 20b are curved and the deformation of the arms 25, 26 is at its least when at the ends of the grooves 19a, 19b; 20a, 20b, the top plate 3 is biased and retained in this first position.

A distal femoral alignment guide is placed into the notch of the femur and the distal femoral outrigger inserted into the alignment guide so that the distal cutting block 1 abuts and rests on the resection portion of the anterior cortex. When the distal cutting block 1 is flat on the anterior cortex, the cutting block 1 is pinned onto the femur by means of the pins 38 inserted through the relevant pin holes 7a, 7b; 8a, 8b and into the bone of the femur 40 in accordance with known surgical techniques. The distal femoral outrigger is the removed from the distal femoral alignment guide and distal cutting block 1.

The alignment guide and outrigger are known devices and, in so far as they do not form part of the present invention, need not be described in any further detail herein. The use of alignment guides and outriggers in knee replacement surgery is described, for example, in "LCS® Surgical Technique" Product Information Sheet by De Puy International and dated 2010.

Before the distal femoral resection can be carried out the extension gap between the femur and the tibia needs to be assessed.

To do this, the top plate 3 of the distal cutting block 1 needs to be moved to the second position. This is achieved, again by manual pressure on the top plate 3 and by use of the buttons 33, 34, if required. The distal surface 37 of the cutting block 1 now represents the level of the cut for the distal femoral resection and can be used to assess the extension gap when used fully extended.

This extension gap must equal the flexion gap and this is done using a spacer block (not shown) in accordance with known techniques. If the spacer block is parallel and aligns with the tibial cut while medial and lateral tissues are equally tensioned then the distal cutting block 1 is correctly located.

The distal cutting block 1 can be positioned using a different row of holes 7a, 7b; 8a, 8b to resect a greater or lesser amount of distal femur to ensure the spacer block will fit in the extension gap. Once the distal cutting block 1 is in the correct position then distal femoral resection can be carried out.

In order to carry-out the resection, the top plate 3 can be in the first position or the second position depending upon which guide surface 37, 39 the surgeon has chosen to use—either the distal surface 37 or the inner guiding surface 39. Again, this is achieved by manual pressure applied to the top plate 3 and buttons 33, 34 as required.

The resection is performed using a saw blade inserted through the gap between the top plate 3 and the cutting block body 2 if the inner guiding surface 39 is being used by the surgeon; otherwise the surgeon uses the distal surface 37 as the surface to guide resectioning of the femur.

Once the resection has taken place, then the cutting block 1 can be removed.

The invention claimed is:

1. A cutting block for fixing relative to a bone for guiding a saw blade during a step in an orthopedic surgical procedure in which the bone is cut, the cutting block comprising:
   a. a body having a wall and a top surface for guiding a saw blade,
   b. a top plate which is connected to the body and which can move between a first position in which the top plate is spaced apart from the body and a second position in which the top surface of the top plate is contiguous with and an extension of the top surface of the body,
   in which the top plate has first and second resiliently deformable arms extending from it, spaced apart along the top plate, in which each of the first and second arms has a pin extending transversely from it, and in which the body has first and second recesses formed in it extending substantially perpendicularly to the top surface of the body, in which the first and second arms on the top plate can be received so that the arms and the recesses define the path for movement of the top plate relative to the body between the first and second positions,
   in which each of the recesses has a profiled surface provided by a curved continuous groove in the wall of the body, and against which the respective deformable arm acts during movement of the top plate relative to the body between the first and second positions so as to cause the arm to deform, the deformation of each of the arms being greater when the top plate is in an intermediate position between the first and second positions than when it is in each of the first and second positions, so that the top plate is biased away from the intermediate position towards the first and second positions;
   in which each pin is received in one groove when the top plate is in the first position, second position and intermediate position;
   and in which each pin slides within one of the grooves as the top plate is moved between first position and second position;
   and in which each of the grooves is curved when viewed in a direction that is defined by the pine that slides in the groove.

2. The cutting block of claim 1, wherein the top surface includes a raised lip and a pair of projections configured to define an inner guiding surface.

3. The cutting block of claim 2, wherein the top surface includes a recess configured to accommodate the raised lip and a pair of apertures configured to receive respective ones of the pair of projections.

* * * * *